United States Patent
Manhart

(10) Patent No.: US 10,932,743 B2
(45) Date of Patent: Mar. 2, 2021

(54) DETERMINING IMAGE VALUES IN MARKED PIXELS OF AT LEAST ONE PROJECTION IMAGE

(71) Applicant: Siemens Healthcare GmbH, Erlangen (DE)

(72) Inventor: Michael Manhart, Fürth (DE)

(73) Assignee: Siemens Healthcare GmbH, Erlangen (DE)

(*) Notice: Subject to any disclaimer, the term of this patent is extended or adjusted under 35 U.S.C. 154(b) by 84 days.

(21) Appl. No.: 16/435,319

(22) Filed: Jun. 7, 2019

(65) Prior Publication Data
US 2019/0374187 A1    Dec. 12, 2019

(30) Foreign Application Priority Data
Jun. 8, 2018  (EP) .................................... 18176803

(51) Int. Cl.
*A61B 6/00* (2006.01)
*G06N 20/00* (2019.01)
(Continued)

(52) U.S. Cl.
CPC .......... *A61B 6/5205* (2013.01); *A61B 6/4441* (2013.01); *G06N 3/08* (2013.01);
(Continued)

(58) Field of Classification Search
CPC ............. G06T 7/97; G06T 2207/30004; A61B 2090/376; A61B 1/0005
See application file for complete search history.

(56) References Cited

U.S. PATENT DOCUMENTS 6,639,596 B1 * 10/2003 Shum ..................... G06K 9/209
                                                                    345/427
7,512,250 B2 * 3/2009 Lim ................... G06K 9/00771
                                                                    382/103
(Continued)

FOREIGN PATENT DOCUMENTS

DE        102017200282 B3    2/2018

OTHER PUBLICATIONS

Aichert, André, et al. "Epipolar consistency in transmission imaging." IEEE transactions on medical imaging 34.11 (2015): 2205-2219.
(Continued)

*Primary Examiner* — Yosef Kassa
(74) *Attorney, Agent, or Firm* — Lempia Summerfield Katz LLC

(57) ABSTRACT

A method for determining image values in marked pixels of at least one projection image is provided. The at least one projection image is part of a projection image set provided for reconstruction of a three-dimensional image dataset and acquired in each case using a projection geometry in an acquisition procedure. The image values are determined through evaluation of at least one epipolar consistency condition that is to be at least approximately fulfilled, that results from the projection geometries of the different projection images of the projection image set, and that requires the agreement of two transformation values in transformation images determined from different projection images by Radon transform and subsequent derivation as a condition transformation.

15 Claims, 4 Drawing Sheets

(51) Int. Cl.
*G06N 3/08* (2006.01)
*G06T 3/40* (2006.01)
*G06T 11/00* (2006.01)

(52) U.S. Cl.
CPC .......... *G06N 20/00* (2019.01); *G06T 3/4007* (2013.01); *G06T 11/006* (2013.01); *G06T 11/008* (2013.01)

(56) References Cited

U.S. PATENT DOCUMENTS

| | | | | |
|---|---|---|---|---|
| 8,175,412 | B2* | 5/2012 | Basri | G06T 7/593 382/278 |
| 8,384,468 | B2* | 2/2013 | Praveena | H03K 19/00369 327/538 |
| 8,781,167 | B2* | 7/2014 | Hu | G06T 7/77 382/103 |
| 9,214,023 | B2* | 12/2015 | Berlinger | G06T 7/74 |
| 2018/0192985 | A1 | 7/2018 | Maass | |

OTHER PUBLICATIONS

Meyer, Esther, et al. "Normalized metal artifact reduction (NMAR) in computed tomography." Medical physics 37.10 (2010): 5482-5493.

Preuhs, Alexander, Michael Manhart, and Andreas Maier. "Fast epipolar consistency without the need for pseudo matrix inverses." arXiv preprint arXiv:1806.02637 (2018). pp. 1-4.

Ronneberger, Olaf, Philipp Fischer, and Thomas Brox. "U-net: Convolutional networks for biomedical image segmentation." International Conference on Medical image computing and computer-assisted intervention. Springer, Cham, 2015. pp. 1-8.

Unberath, Mathias, et al. "Deep learning-bases inpainting for virtual DSA." IEEE Nuclear science symposium and medical imaging conference. 2017. pp. 1-3.

Würfl, Tobias, et al. "A new calibration-free beam hardening reduction method for industrial CT." (2018). pp. 1-7.

European Search Report for related European Patent Application No. 18176803.7, dated Nov. 30, 2018.

* cited by examiner

FIG 4
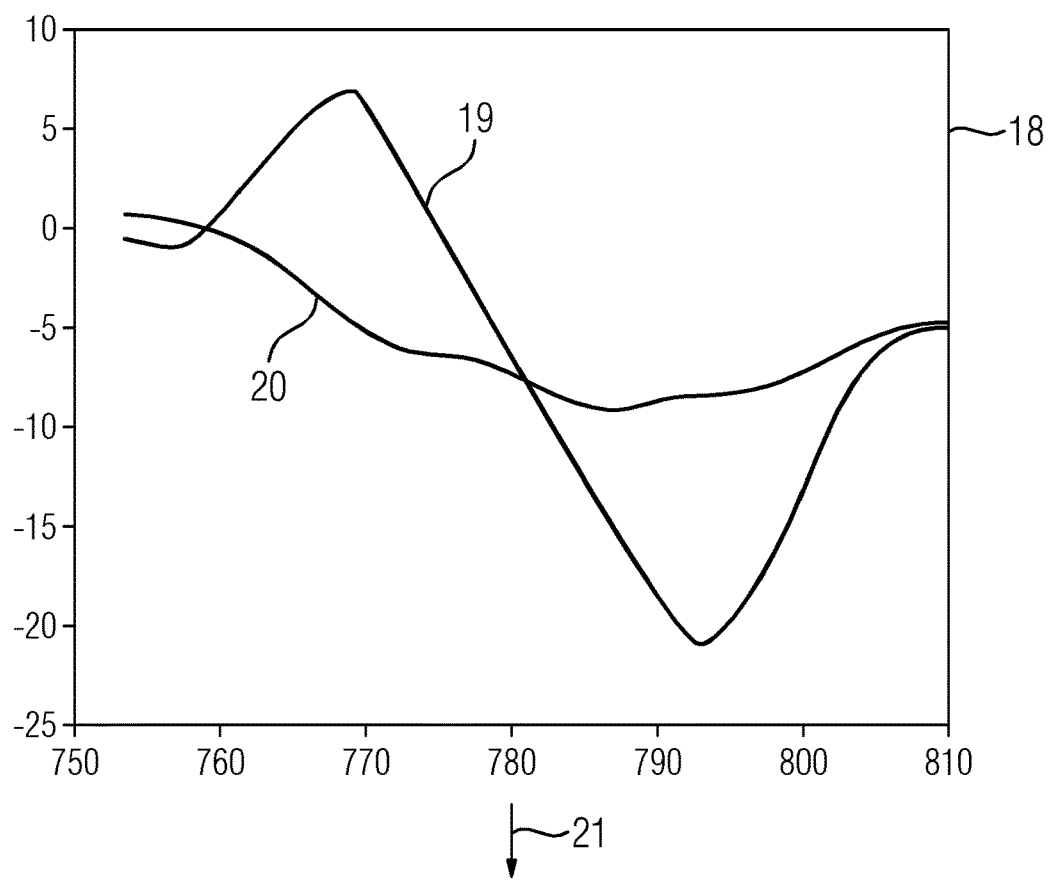
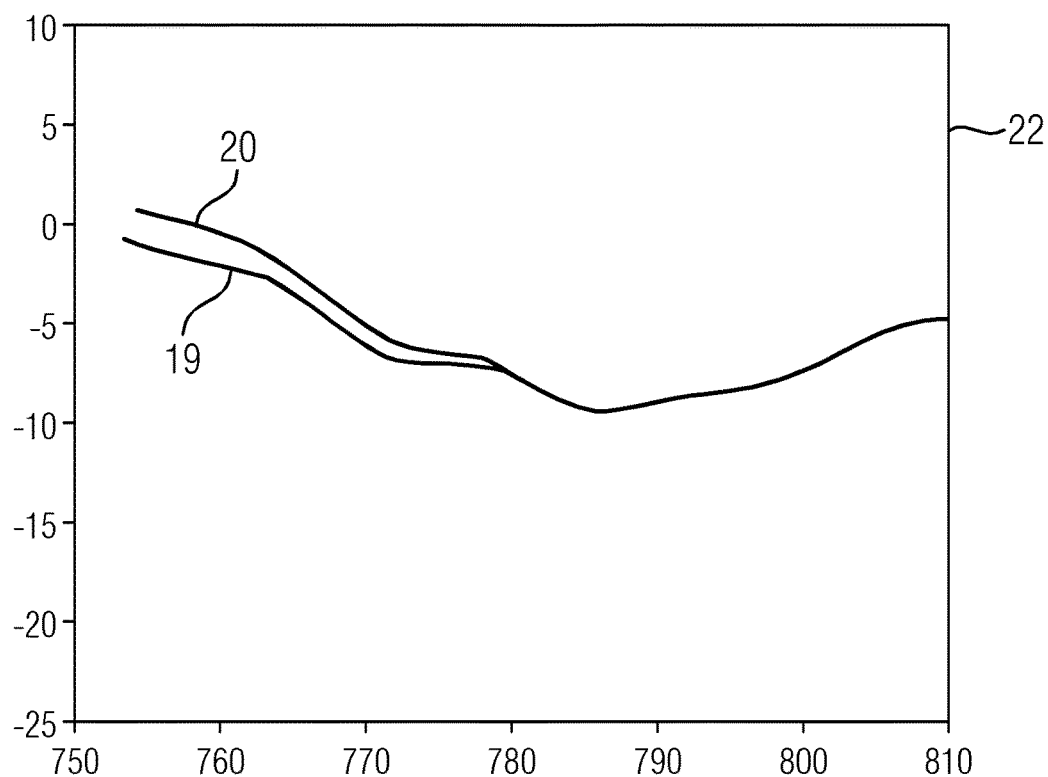

DETERMINING IMAGE VALUES IN MARKED PIXELS OF AT LEAST ONE PROJECTION IMAGE

This application claims the benefit of EP 18176803.7, filed on Jun. 8, 2018, which is hereby incorporated by reference in its entirety.

BACKGROUND

The present embodiments relate to determining image values in marked pixels of at least one projection image.

It has become established practice in, for example, medical X-ray imaging to generate three-dimensional image datasets of an examination region of a patient based on an initial acquisition of X-ray projection images (e.g., along a circular trajectory) using different projection geometries. These two-dimensional (2D) X-ray projection images may be drawn upon as a basis for the reconstruction of a three-dimensional image dataset of the examination region (e.g., using the filtered backprojection method and/or the iterative (algebraic) reconstruction method). For example, 200 to 500 projection images may be acquired in this way using different projection geometries (e.g., projection angles) in the course of a circular path around the examination region of the patient, which, for example, may cover an angular interval of 180° plus the fan angle. A corresponding procedure is employed in computed tomography, for example.

The presence of metals in the examination region may seriously undermine the image quality of the three-dimensional image dataset. Anomalies known as metal artifacts may occur, for example. In order to improve the image quality and to eliminate metal artifacts, it has been proposed to remove the metallic objects in the examination region from the projection data of the projection image set by computational device, which provides replacing the image values indicating metal with image values such as would be approximately expected there without the presence of the corresponding metal object in the examination region. Such a procedure is also known as metal artifact reduction (MAR).

Various approaches for reducing metal artifacts are already well-known in the prior art. Thus, for example, it has been proposed to perform an interpolation within the projection images across the image regions indicating metal. However, an interpolation of the type lacks precision (e.g., in the case of truncated volumes; when the projection images are acquired by an X-ray device having a C-arm), thus leading to a further degradation in image quality.

In an article by Esther Meyer et al. titled "Normalized metal artifact reduction (NMAR) in computed tomography," Medical Physics 37, 5482 (2010), a technique known as normalized metal artifact reduction, in which metal objects are segmented in the three-dimensional image dataset by a thresholding method, for example, was introduced. The pixels indicating metal may be identified in the projection images by a forward projection. Before the interpolation, the projection images are normalized based on a 3D forward projection of a prior image that may be generated by a multithreshold segmentation of the original image. The original raw data is divided by the projection data of the prior image and denormalized again following the interpolation. However, the normalized metal artifact reduction requires a laterally untruncated scan of the object for the normalized interpolation act, since in this case, the values to be interpolated are estimated from numerically projected beams through the examination region.

In addition to interpolation methods of the aforesaid type, methods based on artificial intelligence have also been considered for estimating missing image values, as has been proposed, for example, for estimating mask images in coronary DSA imaging in an article by Mathias Unberath et al. titled "Deep Learning-based In-Painting for Virtual DSA," IEEE Nuclear Science Symposium and Medical Imaging Conference, 2017. In this approach, the background pixels overlaid by contrast agent are estimated with the aid of a convolutional neural network (CNN) using the U-Net architecture (cf. in this regard also the article by Olaf Ronneberger et al. titled "U-Net: Convolutional Networks for Biomedical Image Segmentation," Medical Image Computing and Computer-Assisted Intervention (MICCAI) 9351, pages 234-241 (2015)).

Clearly, "missing" image values for pixels of a projection image may also be usefully determined in a multiplicity of other application cases in addition to metal artifact reduction, where a further application case may also relate to defective individual detectors (pixels) of an X-ray detector, such that the determination or replacement of image values of individual pixels of a projection image may also be referred to generally as "defective pixel estimation" (DPE). The methods used for determining the image values are also referred to as inpainting methods.

In an article by André Aichert et al. titled "Epipolar Consistency in Transmission Imaging," IEEE Transactions on Medical Imaging 34 (2015), pages 2205-2219, the epipolar consistency conditions (ECCs) were derived as a mathematical description of redundancies in the projection images corresponding to the projection geometries. Following a linear transformation (e.g., condition transformation), which is formed by a Radon transform followed by a derivation along the distance coordinate, certain transformation values are required to be the same in two transformation images resulting from projection images. In this situation, the coordinate pairs of the identical transformation values in each case may be calculated for the epipolar consistency conditions from the projection geometries, which may be described, for example, by projection matrices. Given correct acquisition of projection images of an examination region, all of the epipolar consistency conditions are fulfilled. With regard to the epipolar consistency conditions, it has already been proposed to realize a motion correction by a search for displacements of matching values in the transformation images.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an approach to the high-quality supplementing or replacement of image values in inpainting methods is provided.

In one embodiment, in a method, the image values are determined through evaluation of at least one epipolar consistency condition that is to be at least approximately fulfilled, that results from the projection geometries of the different projection images of the projection image set, and that requires the agreement of two transformation values in transformation images determined from different projection images by Radon transform and subsequent derivation as a condition transformation.

It has been shown within the scope of one or more of the present embodiments that in conventional inpainting methods (e.g., in the case of the described interpolation approaches and/or in artificial intelligence-based approaches), the epipolar consistency conditions resulting from the projection geometries of the projection image pairs considered in each case may in most cases be regarded as not fulfilled, such that the estimated image values (e.g., in the course of a metal artifact reduction) do not reveal this natural consistency and may be assessed as being of rather low quality. It is therefore proposed to refer to the epipolar consistency conditions (ECCs) already during the determination of the image values to be determined for correspondingly marked pixels in order to provide the respective consistency as far as possible and thus increase the quality of the estimated image values for the marked pixels. The epipolar consistency conditions ultimately describe the consistency of the approximated image values in the Radon space with the other projection images. Multiple epipolar consistency conditions that are intended to be used in the determination of the image values to be determined for the marked pixels may be formulated as a linear equation system since the condition transformation, which is composed of the Radon transform and the derivation along the distance coordinate, represents a linear transformation. As will be explained in more detail below, the correspondingly resulting linear equation system may be solved directly in order to obtain consistent image values or else may be combined as an additional boundary condition/additional optimization target with other inpainting methods or may be added to the methods in order to improve estimation quality. In one embodiment, the linear equation system relates to the projection images and therefore, to the image values that are to be determined and in some cases are known.

Replacing defective image values or estimating and adding missing image values of marked pixels in projection images by inpainting methods affects a plurality of transformation values in the transformation images, while the use of a conventional inpainting method will, with high probability, produce no image values fulfilling the epipolar consistency conditions. However, by taking the epipolar consistency conditions into account in the determination of image values for the marked pixels in at least one projection image of the projection image set, the consistency is as far as possible maintained. For example, the combination of inpainting methods such as interpolation and/or artificial intelligence-based determination algorithms avoids inconsistent estimations and consequently, potential artifacts in the reconstructed three-dimensional image datasets.

In this case, the epipolar consistency conditions may generally be used in a simple and computationally efficient manner for the consistent estimation of image values that are to be determined. The image quality of the three-dimensional image dataset is increased, and artifacts may be avoided or reduced.

The projection images in this case are, for example, medical image data of a patient that has been acquired by an X-ray device (e.g., an X-ray device having a C-arm) or a computed tomography (CT) device and showing an examination region of the patient that is to be scanned accordingly. However, the method may also be applied to other imaging techniques (e.g., using X-ray imaging) or other fields of application, such as materials testing or the like.

In one embodiment, such image values of image regions indicating metal regions in projection images may be used as image values that are to be determined for marked pixels. In this case, the method according to one or more of the present embodiments is therefore a metal artifact reduction method in which metal objects in the examination region that is revealed by the projection images of the projection image set are finally to be "computationally removed", in that the corresponding marked pixels indicating metals or, more precisely, image values of the corresponding marked pixels are to be replaced by new, approximated image values. The corresponding pixels to be marked in the projection images may in this case be identified in the projection geometries, for example, by segmentation of metal objects in a provisionally reconstructed three-dimensional image dataset and subsequent forward projection, while other approaches may be provided. Marked in this context may be a characterization or indication, in whatever form, that permits the marked pixels to be identified or located as such. For example, the pixels to be marked may be erroneous image values that are caused as metal artifacts. Other metal artifact reduction, the approach according to one or more of the present embodiments may be employed whenever image values of marked pixels are to be replaced or are not present and therefore are to be estimated, as may happen, for example, also in the case of defective pixel detectors of an X-ray detector.

A change to or an addition of an image value at a pixel (e.g., a marked pixel) does not always have a significant effect on each of the epipolar consistency conditions resulting from the projection geometries. The knowledge of the effect would be useful for the building of a linear equation system relating to the projection images. An embodiment therefore provides that for each agreement resulting from the projection geometries that is to be required in two transformation images, as the only epipolar consistency condition, the relevance thereof for the marked pixels in the projection images is checked against a relevance condition. Only relevant epipolar consistency conditions, forming a linear equation system, are used in the determination of the image values to be determined. In an embodiment, an impulse function is applied at each pixel of an image value to be determined (e.g., at each marked pixel), and the condition transformation is applied to the thus resulting and otherwise empty test image. The resulting test transformation images are added together for each projection image, and it is checked as the relevance condition whether a test transformation summation value exceeding a threshold value is present at pixels of the summation image of the test transformation images. The pixels are to be evaluated for an epipolar consistency condition. Alternatively or additionally, the impulse response given by the test transformation image is used for constructing the linear equation system. In other words, the condition transformation is applied to impulse functions that are in each case placed individually at the marked pixels (e.g., delta functions). These may manifest, for example, in test images in which the value 1 is present only at the marked pixel that is to be considered (e.g., a defective pixel); the value 0 is present elsewhere. The respective impulse response (e.g., the test transformation image) in each case describes the effect of the respective image value at the corresponding marked pixel on the transformation values of the transformation image (e.g., a weighting that may be used for forming the linear equation system). Since, typically, image values are to be determined for a plurality of marked pixels within each projection image (e.g., in a metal region), the sum total of all of the impulse responses (e.g., of the test transformation images), from which a binary mask for the transformation images may be formed through threshold value comparison with the absolute amount of the sum total, may be determined. The threshold value may be determined, for example, heuristically and/or as a function of the number of marked pixels in a projection image. The binary mask indicates the pixels of the transformation image with transformation values that are significantly affected by the image values of the marked pixels.

This enables epipolar consistency conditions to be selected that actually possess a relevance in terms of the image values to be determined in the marked pixels. In this way, epipolar consistency conditions that are less relevant or not relevant at all may be excluded from consideration, thus enabling a further estimation of the image values that are to be determined in an efficient and economical manner.

In the special case (e.g., tending to occur rarely in practice), where marked pixels are present only for one projection image of the projection image set, "correct" transformation values from other projection images are basically present for each epipolar consistency condition (e.g., each relevant epipolar consistency condition). In the case in which marked pixels are present in a plurality or all of the projection images (e.g., when imaging a metal object in the examination region), other image values to be determined for other projection images may have an effect on a comparative transformation value resulting from a projection image and required transformation value relevant to an epipolar consistency condition, such that a considerably more complex linear equation system results. This provides that a comparative transformation value of the corresponding epipolar consistency condition that is unaffected by image values to be determined may not be derived for every transformation value that is affected by an image value to be determined.

As already mentioned, the great advantage in the consideration of impulse responses for individual marked pixels is the resulting knowledge about the contribution made by the marked pixel to transformation values possibly forming part of an epipolar consistency condition. In order to build the linear equation system in the space of the projection images in the case of impulse responses present as test transformation images, a matrix describing the effect of the to be determined image values of the respective marked pixels on the transformation values contained in the epipolar consistency conditions to be used in each case (e.g., relevant) may therefore be determined for each projection image containing marked pixels and used to formulate the linear equation system.

Within the scope of one or more of the present embodiments, it is possible that the image values to be determined are determined by solution of the equation system formed by the epipolar consistency conditions that are to be used. If the overall intention is rather to determine a small number of image values for marked pixels (e.g., in the case of "defective" pixels in only one or very few projection images of the projection image dataset), a linear equation system that is solvable or even overdetermined may be produced by the epipolar consistency conditions. Specifically, in application areas frequently occurring in practice, however, (e.g., in metal artifact reduction), marked pixels, and consequently image values to be determined, occur in all projection images of the projection image dataset, with the result that unknown image values may stand on both sides in the linear equation system. With higher probability, this makes the linear equation system underdetermined. However, even for underdetermined linear equation systems of the type, there still exist solution methods in order to enable a benign, meaningful solution to be found in the form of image values to be determined.

Thus, it may be provided, for example, that in the case of an underdetermined equation system, a Tikhonov regularization and/or at least a prior knowledge about the boundary condition using the image values may be determined. In the known Tikhonov regularization, a predefinition of characteristics of the obtained solution may be incorporated into the linear equation system via the choice of the Tikhonov matrix. In one embodiment, a solution using little energy and/or a solution having few additional edges may be aimed for. As well as the Tikhonov regularization, other methods may be used in order to introduce boundary conditions that ultimately describe background knowledge relating to the existing or wanted behavior within regions of marked pixels that are to be replaced.

In one embodiment, the epipolar consistency conditions as a boundary condition and/or an optimization target may be added to a generally known or conventional inpainting method, such that an embodiment provides that the epipolar consistency conditions to be used are used as boundary conditions and/or as an optimization target for at least one determination algorithm for determining the image values to be determined. In this case, therefore, a determination algorithm that does not solve the linear equation system but attempts to estimate image values of the marked pixels in a different way is used. In the process, the determination algorithm may be aimed, for example, at an interpolation and/or at the use of artificial intelligence.

In an embodiment, an artificial intelligence algorithm trained by machine learning (e.g., deep learning) is used as the determination algorithm. In one embodiment, for determination algorithms that are to estimate missing image values or image values to be replaced in marked pixels, it is often very well possible to draw upon high-quality training data, for example, in the case of metal artifact reduction, through generation of a projection image set that shows a subject without metal objects or by acquisition of images of an examination region with and without metal object. In this way, the ground truth is then available in any case. In one embodiment, in this connection, if the determination algorithm includes a neural network (e.g., a convolutional neural network (CNN)) in U-Net architecture. The linear equation system produced as a result of the epipolar consistency conditions may be particularly easily integrated (e.g., in the case of neural networks), since the epipolar consistency conditions contain a linear weighting followed in each case by an (optional) nonlinear operator that greatly simplifies an integration of the linear equation system into the neural network and brings with it a direct benefit. This provides that the use of the epipolar consistency conditions appears particularly useful in a combination with inpainting methods based on machine learning (e.g., deep learning).

In this case, independently of the use of epipolar consistency conditions, the use of CNN (e.g., in U-Net architecture), as described by the articles by Unberath et al. and Ronneberger et al. cited in the introduction, represents an extremely useful approach for estimating image values to be determined (e.g., also in the case of laterally truncated scans of an examination region of a patient). In the use of such artificial intelligence-based determination algorithms or specifically of CNNs, an image section around the marked pixels (e.g., a metal object) may be used with the masked image values of the marked pixels as input data, whereupon the determination algorithm delivers an image containing the estimated image values for the marked pixels as output. The "metal values" in the input image are then replaced by the estimated image values in the output image. By this, image values may be estimated for a wide diversity of metal shapes provided the metal object is smaller than the image section.

It may further be provided within the scope of the present embodiments that the determination algorithm performs an interpolating determination of the image values to be determined (e.g., in accordance with the normalized metal artifact reduction (NMAR) method). In this case, for example, a forward projection of an initially corrected volume may be called upon for an improved interpolation, in which case, however, a consistent estimation in accordance with the epipolar consistency conditions is not guaranteed. With this respect, the use of the epipolar consistency conditions as proposed here may also lead in combination with NMAR to substantially improved estimations for marked pixels.

The method described may be performed by a computing device, though, for example, also by a control device of an X-ray device, such that appropriate measures for replacing and/or supplementing erroneous image values that are to be removed and/or missing image values may already be provided on the X-ray device itself.

In addition to the method, the present embodiments also relate to an X-ray device including a control device embodied to perform the method. All statements made in relation to the method according to the present embodiments may be applied analogously to the X-ray device, by which the already cited advantages may therefore likewise be obtained. For example, the X-ray device may be an X-ray device having a C-arm on which an X-ray source and an X-ray detector are arranged opposite each other. Alternatively, the X-ray device may be a computed tomography device in which, for example, at least one X-ray source and X-ray detector pair disposed within a gantry may be moved around the patient. The control device of such an X-ray device may be configured to estimate image values of marked pixels in the manner according to one or more of the present embodiments, which provides useful, high-quality functions for increasing the image quality of acquired image data and, for example, of three-dimensional image datasets already at the X-ray device itself. The control device may include at least one processor and/or at least one storage device and/or include a determination unit in order to determine image values to be determined using epipolar consistency conditions.

A computer program according to one or more of the present embodiments may, for example, be loaded directly into a memory of a computing device (e.g., a control device of an X-ray device), and has a program in order to perform the acts of a method described herein when the computer program is executed in the computing device. The computer program may be stored on an electronically readable data medium (e.g., a non-transitory computer-readable storage medium) according to one or more of the present embodiments. The computer program therefore includes electronically readable control information (e.g., instructions) stored thereon that includes at least one computer program and is embodied to carry out a method when the data medium is used in a computing device (e.g., in a control device of an X-ray device). The data medium may be a non-transitory data medium (e.g., a CD-ROM).

BRIEF DESCRIPTION OF THE DRAWINGS

FIG. 4 shows a schematic diagram intended to improve the fulfillment of epipolar consistency conditions.

DETAILED DESCRIPTION

Exemplary embodiments of the method are presented below in relation to medical imaging and, more specifically, to metal artifact reduction in three-dimensional X-ray image datasets that are to be reconstructed. In this regard, as is generally known, a plurality of projection images of an examination region of the patient are acquired by an X-ray device using different projection geometries, each of which is described by a projection matrix (e.g., along a circular scanning trajectory). The projection images form a projection image set. Using the projection images, by applying corresponding reconstruction methods (e.g., filtered back-projection), a three-dimensional image dataset may be reconstructed from the two-dimensional projection images. This may, however, lead to artifacts if metal objects are present in the examination region. Metal objects, and consequently the cause of the metal artifacts, may therefore be computationally removed from the projection images by replacing corresponding image values indicating the metal object in pixels of the respective projection images correspondingly marked as showing the metal object by estimated image values without the metal object. The marked pixels, which may be determined, for example, as a result of a segmentation of the metal object in a provisionally reconstructed three-dimensional image dataset, may also be referred to as "defective" pixels for which an image value (e.g., a replacement image value) is to be found. Within the scope of one or more of the present embodiments, epipolar consistency conditions, as described in the article by Aichert et al. cited in the introduction, are taken into account where appropriate, in addition to other inpainting methods, for the purpose of estimating the image values in the marked pixels.

Figure 1:
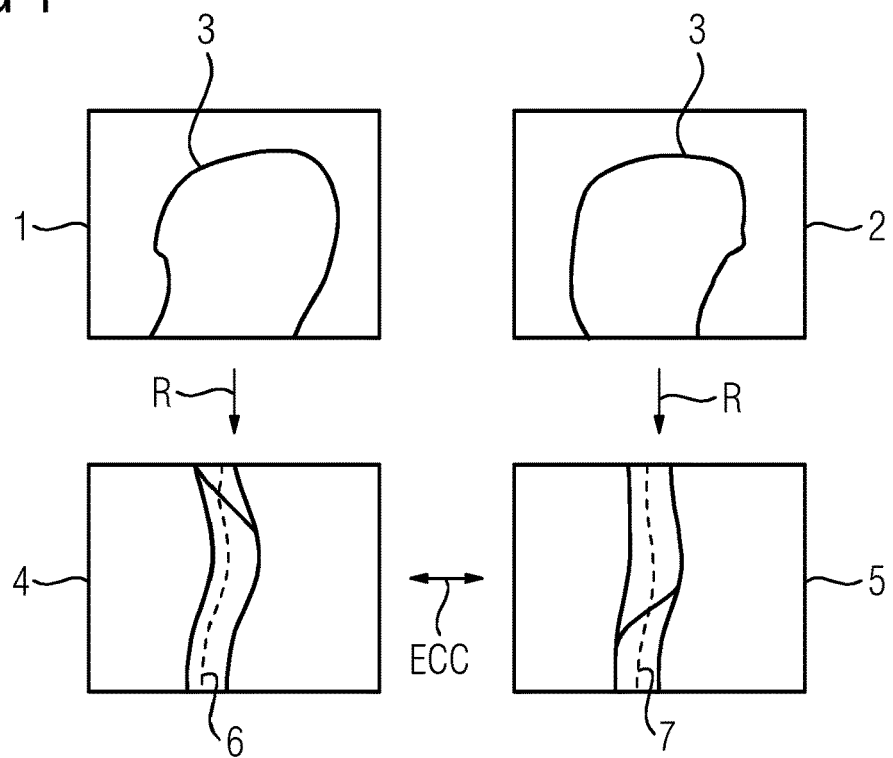
FIG. 1 shows a schematic diagram that illustrates epipolar consistency conditions.

In order to explain the epipolar consistency conditions, FIG. 1 shows two projection images 1, 2 of an examination region of a patient acquired using different projection geometries. The two projection images 1, 2 show, as is generally known, anatomical structures 3 of the patient from different viewing directions. If the cosine-weighted image values of the projection images 1, 2 are designated as $p_\lambda$, where $\lambda$ represents a running index of the projection images 1, 2, the Grangeat's intermediate function r, corresponding to a transformation image 4, 5 is yielded as $$r_\lambda = R p_\lambda,$$

where the transformation R referred to in the following as a condition transformation includes a Radon transform (e.g., discretized), followed by a derivation along the distance coordinate.

If, in the example presented here concerning the projection matrices, the projection geometries of the projection images 1, 2 are now known, it may be derived herefrom that transformation values of specific pixels of the transformation images 4, 5 are to be consistent with one another in formulae if the corresponding coordinates of the determined pixels are designated as ECC (1, 1) for the transformation image 4 and as ECC (1, 2) for the transformation image 5, and k is the number of epipolar consistency conditions:

$$r_{\lambda,1}(\text{ECC}(l,1)) = r_{\lambda,2}(\text{ECC}(l,2)) \text{ where } l=1 \ldots k.$$

The dashed lines 6, 7 in FIG. 1 may, for example, describe where such epipolar consistency conditions may occur in the transformation images 4, 5. In other words, the dashed line 6 corresponds to the sequence of the coordinates ECC (1, 1), and the dashed line 7 corresponds to the sequence of the coordinates ECC (1, 2).

Under perfect acquisition conditions, the epipolar consistency conditions apply exactly. If, however, image values estimated in marked pixels are now inserted in one or both of the projection images 1, 2 (e.g., due to a metal object), these will, with high probability, not be fulfilled without the epipolar consistency conditions being taken into account. However, the epipolar consistency conditions describe the consistency in the Radon space, such that in determining estimated image values for marked pixels using the epipolar consistency conditions or at least some of the existing epipolar consistency conditions that are relevant to the marked pixels, a significantly higher-quality estimation is achieved with less susceptibility to artifacts as a result of the replacement of the metal object.

Figure 2:
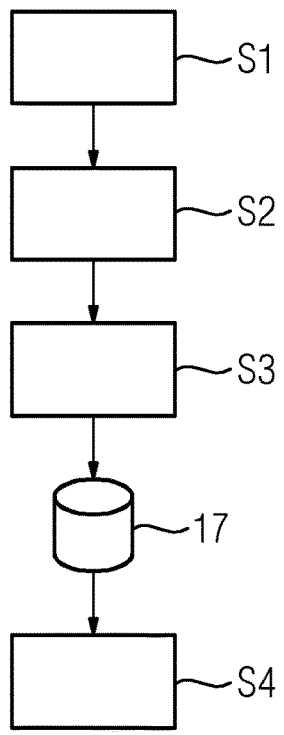
FIG. 2 shows a schematic flowchart of exemplary embodiments of a method.

FIG. 2 shows in this regard a general flowchart of exemplary embodiments of the method according to one or more of the present embodiments. It is aimed initially to determine which epipolar consistency conditions that may be formulated for a projection image set possess any relevance for the problem posed (e.g., estimating image values for specific marked ("defective") pixels in some or all projection images 1, 2 of the projection image set).

In act S1, a number of test images are generated for each projection image. The number corresponds to the number of marked pixels in the respective projection image. The test images finally correspond to an impulse function that is positioned at one marked pixel in each case. In the present example, the test images are generated such that a value of 1 is present at the marked pixel; a value of 0 is present everywhere else. If the test images are now subjected to the condition transformation R, the result yielded indicates what effect the image value of the corresponding marked pixel has on which pixels of the transformation image. The condition transformation R is therefore applied to the respective corresponding test images in act S1 of FIG. 2 in order to obtain test transformation images.

Figure 3:
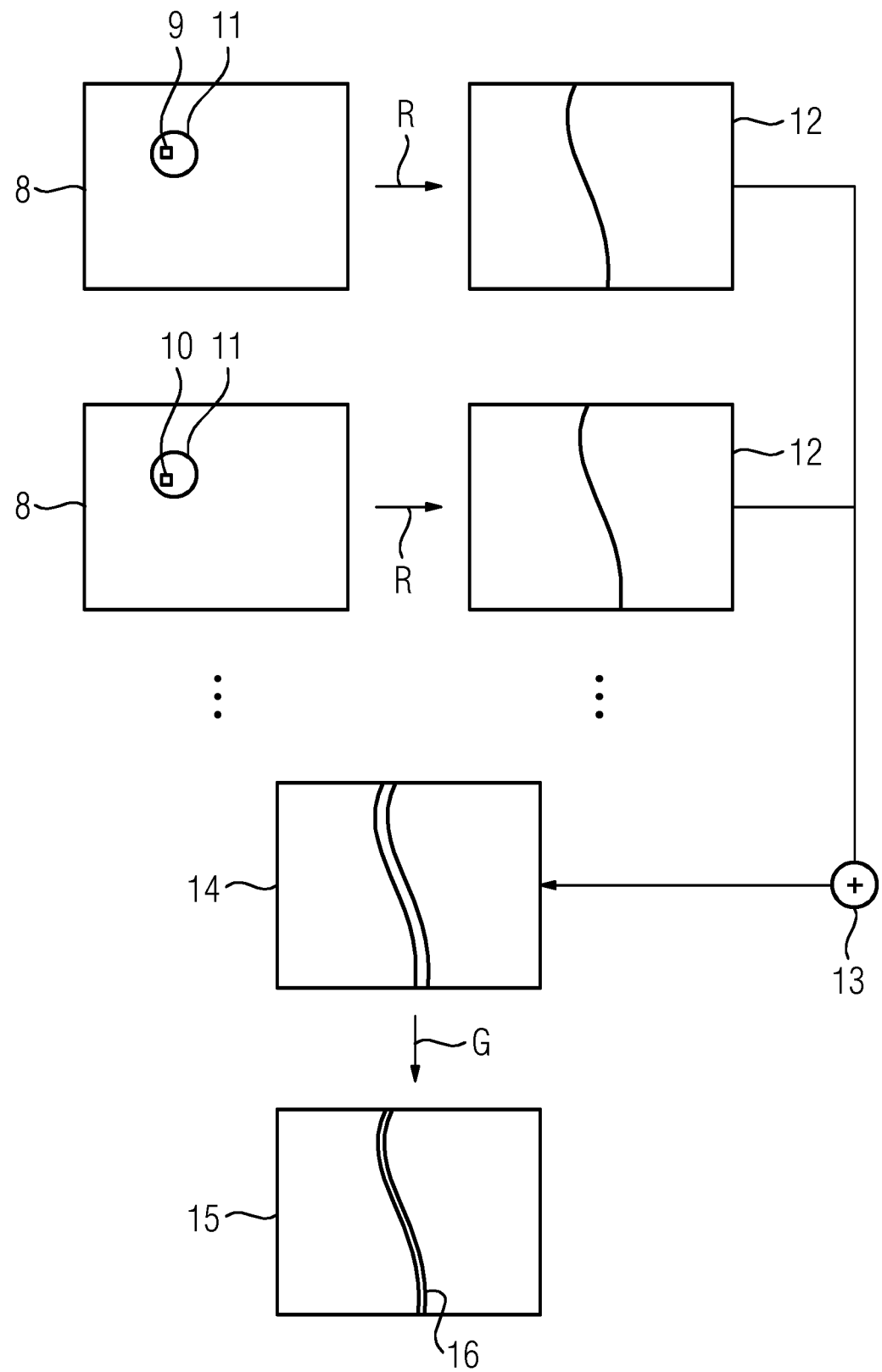
FIG. 3 shows a schematic diagram that illustrates the use of relevance conditions.

This procedure is illustrated once again graphically by FIG. 3 for one of the projection images of the projection image set. Initially to be seen are test images 8, each of which relates to a different marked pixel 9, 10 within the region 11 of marked pixels of a specific projection image (e.g., one of the projection images 1, 2). The continuation points indicate that corresponding test images 8 are generated as impulse functions for all marked pixels in the region 11. The condition transformation R is then applied to each of the test images 8 in order to obtain test transformation images 12.

In order to obtain an assessment of the effect of all of these marked pixels 9, 10 on general transformation images, the corresponding resulting test transformation images 12 are added together in act S2 according to FIG. 2 for each of the projection images, as is illustrated by the operation 13 in FIG. 3. The result is a summation image 14, to which, still in act S2, a threshold value comparison with a threshold value G is applied in order to generate a binary mask 15. The threshold value G may be dependent on the number of marked pixels in the respective projection image and/or be determined heuristically. The binary mask 15 substantially indicates on which transformation values image values of the marked pixels 9, 10 have a relevant effect.

Accordingly, the binary mask 15 may be used in act S3 in order to identify relevant epipolar consistency conditions. For this purpose, coordinates of pixels in the transformation images 4, 5 of respective pairs of projection images 1, 2 for which epipolar consistency conditions may be formulated, are determined, and the binary mask 15 is linked to the coordinates (ECC(1, ½)). The epipolar consistency conditions for which at least one of the corresponding coordinates lies within the relevance region 16 indicated by the binary mask (cf. FIG. 3) are therefore selected.

These relevant epipolar consistency conditions are now used in conjunction with the impulse responses determined as test transformation images 12 in order to form, as the result of acts S1 to S3, a linear equation system 17 (cf. FIG. 2) that is used in a following act S4 in the determination of the image values for the marked pixels 9, 10.

In order to form the linear equation system 17, the known effects of the individual marked pixels 9, 10 on the transformation values (e.g., relevant transformation values) for each transformation image are used to formulate the linear equation system directly for the image values to be determined. In this case, matrices that describe the effect on the transformation values contained in the relevant epipolar consistency conditions are produced for each projection image in which marked pixels 9, 10 are present.

For illustration purposes, this is explained in more detail with the aid of a simple example in which marked pixels 9, 10 are present in one projection image only, whereas all others are completely known. This provides that only one side of the epipolar consistency conditions then has unknowns (e.g., image values to be determined).

k is the number of relevant epipolar consistency conditions identified in act S3, and l is the number of marked pixels in the projection image l1. If, in addition, the impulse response (e.g., the test transformation values of the associated test transformation image 12 for a marked pixel v) is designated by $IRS_v$, then the IRSs are in each case m-dimensional vectors (e.g., m=total number of pixels). If the matrix $$W(u,v)=IRS_v(i_{u,1})$$

is defined, where $i_{u,1}$ describes the coordinates of the pixel of the transformation image from the projection image l1 at which the transformation value of the epipolar consistency condition u is to be read off, then the matrix W lies in the k×l-dimensional space.

If the vector $$y(u)=r_{l(u)}(i_{u,2})-r_{l1}(i_{u,1})$$

is defined in the k-dimensional space, where l(u) describes the projection image belonging to the epipolar consistency condition u, $i_{u,2}$ describes the coordinate of the corresponding transformation value, and r describes the transformation values. y(u) therefore describes the deviation from the validity of the epipolar consistency condition u.

The solution set x in the one-dimensional space of the linear equation system W x=y then describes the consistent image values to be determined.

If, as in the usual cases, marked pixels 9,10 are present in a plurality of or all projection images, unknowns and corresponding matrices W occur on both sides of the epipolar consistency conditions, with the result that the equation system 17 is more complicated than presented here, but may be determined in the same way.

The solution set of the linear equation system 17 describes the image values to be determined for the marked pixels 9, 10, which are consistent with the respective other projection images of the projection image set. The linear equation system 17 may be used in different ways.

In a first embodiment, the linear equation system 17 may be solved in act S4, where a suitable solution may be found even in the case of an underdetermined linear equation system 17 (e.g., through the use of the Tikhonov regularization).

Exemplary embodiments in which the epipolar consistency conditions contained in the linear equation system 17 are added to another inpainting method as boundary condition or as an optimization target to be optimally fulfilled are provided. While it is possible to extend an interpolation method such as normalized metal artifact reduction (NMAR) in order to use the linear equation system 17, artificial intelligence-based determination algorithms (e.g., such that use convolutional neural networks (CNNs) in U-Net architecture) represent an embodiment. This is because linear equation systems may be easily integrated into neural networks on account of the structure of the neural networks. An efficient conversion is produced as a result.

FIG. 4 shows, by way of example, the development of the fulfillment of epipolar consistency conditions in a use of the same as an optimization target. In this example, the top graph 18 shows the characteristic curves 19, 20 of transformation values that, according to relevant epipolar consistency conditions, should correspond to one another. It is clear that significant differences still exist between the individual transformation values of the characteristic curves 19, 20; no good consistency is given in the Radon space.

If, however, the epipolar consistency conditions are incorporated (e.g., in the form of the linear equation system 17) into an optimization process, indicated by the arrow 21, of a determination algorithm, a much better consistency according to the graph 22 is obtained. This provides that the epipolar consistency conditions are fulfilled considerably better. This may be achieved, for example, through the use of a tuple of image values for the marked pixels 9, 10 that lies as close as possible to the solution space of the linear equation system 17 as end result or the end result even lies within the solution space of the linear equation system 17.

Figure 5:
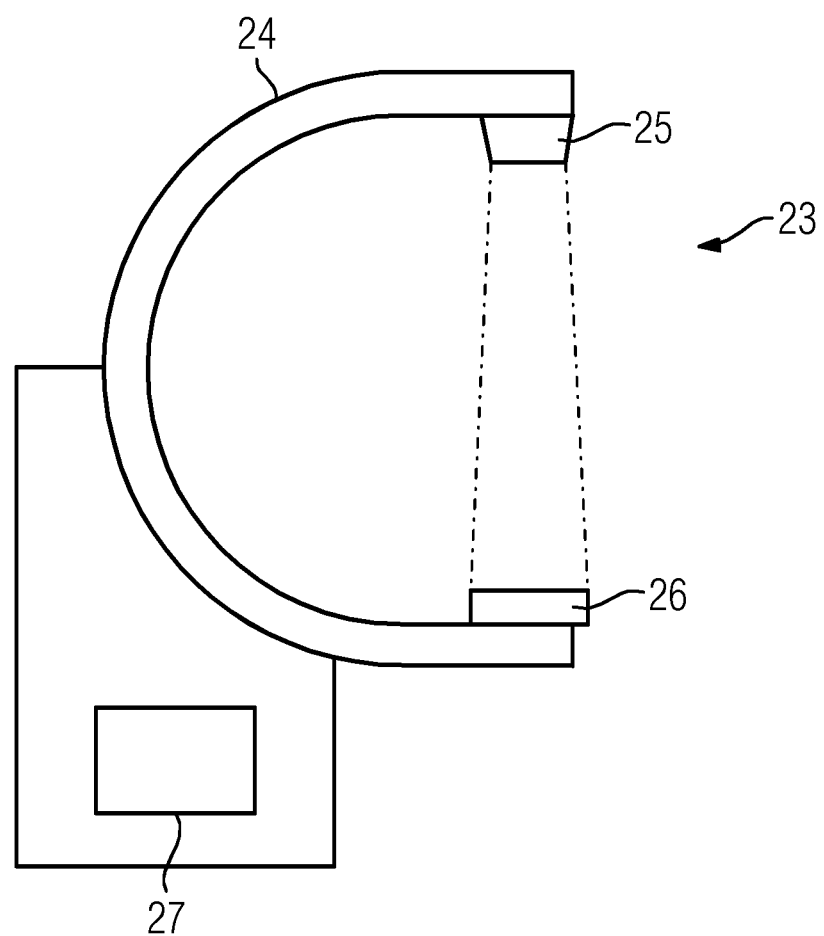
FIG. 5 shows an X-ray device according to an embodiment.

FIG. 5 shows a schematic diagram illustrating an X-ray device 23 according to one or more of the present embodiments, which in the present example, is realized as an X-ray device 23 having a C-arm 24 on which an X-ray source 25 and an X-ray detector 26 are arranged opposite each other. The C-arm 24 is movable and may, for example, be rotated around a patient positioned on a patient couch (not shown here in further detail). This enables projection images 1, 2 to be generated using different projection geometries. The control device 27 of the X-ray device 23 is also embodied for performing the method according to one or more of the present embodiments, which provides that epipolar consistency conditions may be used directly on the X-ray device 23 during the estimation of image values for marked pixels. For this purpose, the control device 27 may include a corresponding determination unit, as well as further subunits and/or functional units where necessary in order to realize the different acts of the method according to one or more of the present embodiments.

Although the invention has been illustrated and described in greater detail based on the exemplary embodiments, the invention is not limited by the disclosed examples. Other variations may be derived herefrom by the person skilled in the art without leaving the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining image values in marked pixels of at least one projection image, wherein the at least one projection image is part of a projection image set provided for reconstruction of a three-dimensional (3D) image dataset and comprising projection images acquired in each case using a projection geometry in an acquisition procedure, the method comprising:

determining the image values through evaluation of at least one epipolar consistency condition that is to be at least approximately fulfilled, that results from projection geometries of the different projection images of the projection image set, and that requires agreement of two transformation values in transformation images determined from different projection images by Radon transform and subsequent derivation as a condition transformation.

2. The method of claim 1, wherein image values of image regions indicating metal regions in projection images are used as image values that are to be determined.

3. The method of claim 1, wherein for each agreement resulting from the projection geometries that is to be required in two transformation images, as the only epipolar consistency condition, the relevance thereof for the marked pixels in the projection images is checked against a relevance condition, and wherein only relevant epipolar consistency conditions, forming a linear equation system, are used in the determination of the image values to be determined.

4. The method of claim 3, wherein an impulse function is applied at each marked pixel, and the condition transformation is applied to the thus resulting and otherwise empty test image, wherein the resulting test transformation images are added together for each projection image, and it is checked as a relevance condition whether a test transformation summation value exceeding a threshold value is present at pixels of the summation image of the test transformation images that are to be evaluated for an epipolar consistency condition, wherein the impulse response given by the test transformation image is used for building the linear equation system; or any combination thereof.

5. The method of claim 3, wherein the image values to be determined are determined by solution of the linear equation system formed by the epipolar consistency conditions that are to be used.

6. The method of claim 5, wherein a Tikhonov regularization, at least a prior knowledge about a boundary condition using the image values to be determined, or a combination thereof is used.

7. The method of claim 6, wherein the Tikhonov regularization, at least the prior knowledge about the boundary condition using the image values to be determined, or the combination thereof is used in the case of an underdetermined equation system.

8. The method of claim 1, wherein the epipolar consistency conditions to be used are used as boundary conditions, as an optimization target for at least one determination algorithm for determining the image values that are to be determined, or as a combination thereof.

9. The method of claim 7, wherein an artificial intelligence algorithm trained by machine learning is used as a determination algorithm of the at least one determination algorithm.

10. The method of claim 8, wherein the determination algorithm comprises a neural network.

11. The method of claim 10, wherein the determination algorithm comprises a CNN in U-Net architecture.

12. The method of claim 7, wherein the determination algorithm performs an interpolating determination of the image values that are to be determined.

13. The method of claim 12, wherein the determination algorithm performs the interpolating determination of the image values that are to be determined in accordance with the normalized metal artifact reduction method.

14. An X-ray device comprising:
a controller configured to:
   determine image values in marked pixels of at least one projection image, wherein the at least one projection image is part of a projection image set provided for reconstruction of a three-dimensional (3D) image dataset and comprising projection images acquired in each case using a projection geometry in an acquisition procedure, the determination of the image values comprising:
   determination of the image values through evaluation of at least one epipolar consistency condition that is to be at least approximately fulfilled, that results from projection geometries of the different projection images of the projection image set, and that requires agreement of two transformation values in transformation images determined from different projection images by Radon transform and subsequent derivation as a condition transformation.

15. In a non-transitory computer-readable storage medium that stores instructions executable by a controller to determine image values in marked pixels of at least one projection image, wherein the at least one projection image is part of a projection image set provided for reconstruction of a three-dimensional (3D) image dataset and comprising projection images acquired in each case using a projection geometry in an acquisition procedure, the instructions comprising:
   determining the image values through evaluation of at least one epipolar consistency condition that is to be at least approximately fulfilled, that results from projection geometries of the different projection images of the projection image set, and that requires agreement of two transformation values in transformation images determined from different projection images by Radon transform and subsequent derivation as a condition transformation.

* * * * *